(12) United States Patent
Koplin

(10) Patent No.: US 9,333,114 B2
(45) Date of Patent: *May 10, 2016

(54) APPARATUS FOR PERFORMING PHACO-EMULSIFICATION

(71) Applicant: FLUIDICS PARTNERS, LLC, New York, NY (US)

(72) Inventor: Richard S. Koplin, New York, NY (US)

(73) Assignee: Fluidics Partners, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/748,481

(22) Filed: Jun. 24, 2015

(65) Prior Publication Data

US 2015/0328048 A1 Nov. 19, 2015

Related U.S. Application Data

(63) Continuation-in-part of application No. 14/197,295, filed on Mar. 5, 2014.

(60) Provisional application No. 61/773,998, filed on Mar. 7, 2013.

(51) Int. Cl.
*A61F 9/007* (2006.01)
*A61M 1/00* (2006.01)
*A61B 17/32* (2006.01)

(52) U.S. Cl.
CPC ..... *A61F 9/00745* (2013.01); *A61B 17/320068* (2013.01); *A61F 9/00763* (2013.01); *A61M 1/0058* (2013.01); *A61B 2017/320072* (2013.01); *A61B 2017/320084* (2013.01); *A61B 2017/320088* (2013.01)

(58) Field of Classification Search
CPC ............ A61F 9/00736; A61F 9/00745; A61F 9/00754; A61B 2017/320072; A61B 2017/320076; A61B 2017/320084; A61M 1/0084; A61M 1/0058
USPC .............................................. 606/107; 604/22
See application file for complete search history.

(56) References Cited

U.S. PATENT DOCUMENTS

| 5,935,096 A * | 8/1999 | Barrett ................ A61F 9/00745 604/22 |
| 2009/0093750 A1* | 4/2009 | Herman .............. A61F 9/00745 604/22 |

* cited by examiner

*Primary Examiner* — Jonathan W Miles
*Assistant Examiner* — George J Ulsh
(74) *Attorney, Agent, or Firm* — Gottlieb, Rackman & Reisman, P.C.

(57) ABSTRACT

An apparatus provides mechanical energy to vibrate a needle. An irrigating sleeve is disposed around the needle and includes one or more irrigation ports through which irrigation liquid is ejected during emulsification. To prevent the needle from occluding the irrigation ports with its deflections, one or more bumpers are provided between the sleeve and the needle.

11 Claims, 4 Drawing Sheets

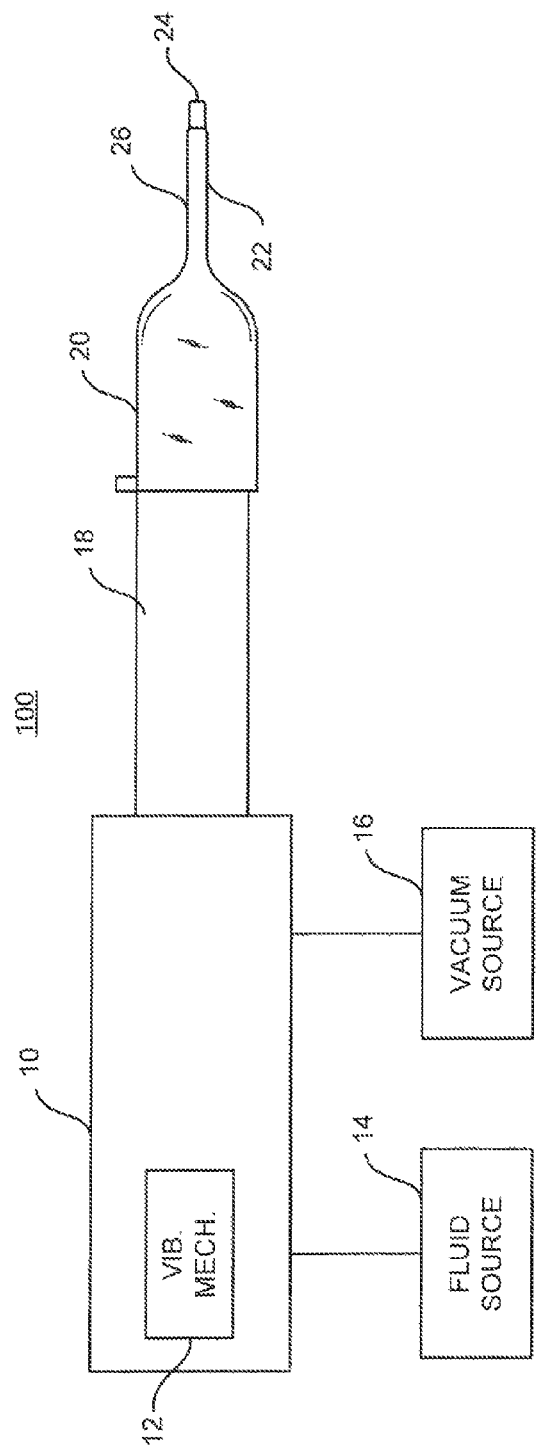
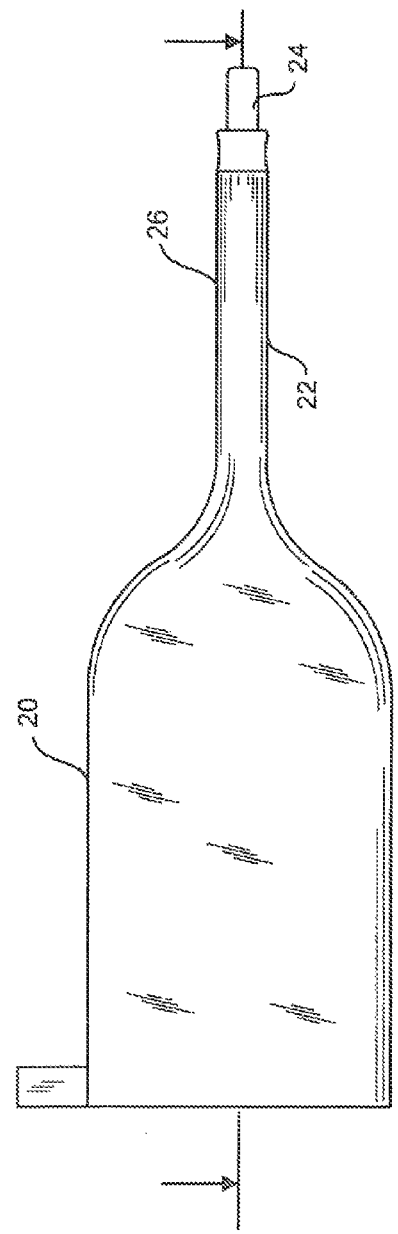
FIG. 1A
FIG. 1B

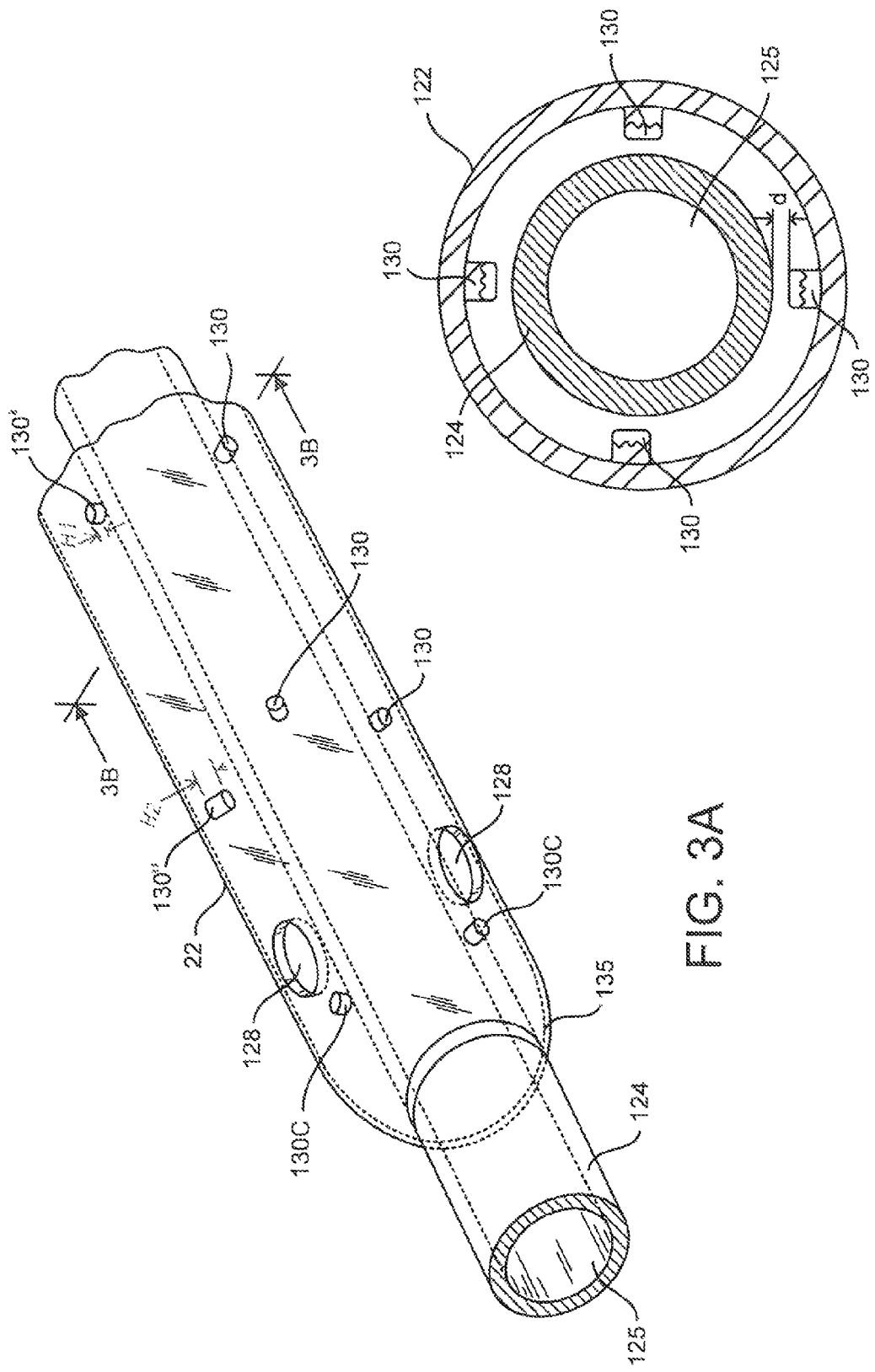

APPARATUS FOR PERFORMING PHACO-EMULSIFICATION

RELATED APPLICATIONS

This application claims priority to and is a continuation-in-part of U.S. application Ser. No. 14/197,295 filed Mar. 5, 2014, now pending, which claims priority to U.S. Provisional Application Ser. No. 61/773,998 filed Mar. 7, 2013, all incorporated herein by reference in its entirety.

BACKGROUND OF THE INVENTION

A. Field of Invention

This invention pertains to an apparatus for performing phacoemulsification using a handpiece including a hollow needle used to pulverize the lens and a sleeve surrounding the needle. Irrigating liquid is injected into the anterior chamber from the sleeve. The sleeve is provided with a plurality of bumpers arranged to minimize deflections of the needle during the emulsification process thereby minimizing obstruction of infusion fluid from the exit ports in the sleeve.

B. Description of the Prior Art

Phaco-emulsification is a procedure used to break up and remove the natural lens from the capsular bag within the eye of a person. Most often the procedure is used as a means of treating a person having cataracts. The procedure involves making a small incision in the eye and introducing through the incision a thin hollow needle having a central passage. A circumferential sleeve surrounds the needle. The needle is coupled to an ultrasonic generator that vibrates the needle in a predetermined (preferably ultrasonic) frequency range causing the natural lens to fragment and emulsify. Irrigation fluid enters the anterior chamber of the eye through two or more ports formed in the outer sleeve surrounding the needle. Detritus resulting from the phaco-emulsification process mixes together with the liquid and is aspired through the central passage in the needle. The liquid used for irrigation also produces a stabilizing effect in the anterior and posterior chambers, keeping the eye inflated.

To complete the operation, an intraocular lens implant is then inserted into the capsular bag (usually through the same incision).

While the technology has for the most part been broadly accepted as the community norm, the present inventor has discovered several disadvantages in the presently available equipment used for phaco-emulsification. It is preferable to have the liquid used for irrigation ejected evenly from ports to insure a relatively smooth, non-turbulent and non-violent fluid flow within the anterior chamber. However the present inventor has discovered that during phaco-emulsification, the needle deflects considerably within the sleeve frequently occludes or blocks one of the ports on the sleeve (at least partially). As a result, since the pressure within the sleeve is fairly constant, the flow of the liquid through one of the ports is reduced temporarily by the deflected needle, the flow through the other port(s) increases suddenly, In other words, while one port is at least partially blocked by the needle, the liquid through the other port is ejected at a greater volume and velocity. This effect is undesirable since it can cause detritus resulting from the phaco-emulsification to be pushed away from the aspiration tip and toward the furthest corners of the anterior chamber, occasionally transporting unwanted lens material to the back of the eye. Additional problems may also occur as a result of uneven liquid flow through the ports. The present invention addresses this problem. It should be understood that during emulsification, the needle deflection changes continuously during emulsification, and it blocks one of the ports only for fractions of a second—often alternating rapidly from one side of the sleeve to the other.

SUMMARY OF THE INVENTION

An apparatus is disclosed that includes a sleeve with one or more ports for ejecting irrigation liquid into the eye of a patient. The apparatus also includes a needle disposed nominally concentrically within the sleeve. The needle is vibrated to provide emulsification. It has been found that the needle deflects in a somewhat random manner by manipulation by the surgeons as it is being vibrated and that, as it deflects, it occludes the ports in the distal sleeve causing undesirable variations in the flow of the irrigation liquid into the eye. In order to prevent, or at least reduce this effect, one or more bumpers are provided between the sleeve and the needle. In one embodiment the bumpers are provided on the inside surface of the sleeve. The heights of the bumpers can be constant or various bumpers can have differing heights.

BRIEF DESCRIPTION OF THE DRAWINGS

FIG. 1A shows a block diagram of an apparatus for performing phaco-emulsification constructed in accordance with this invention;

FIG. 1B shows an enlarged side view of the sleeve of the apparatus of FIG. 1A;

FIG. 3A shows a side orthogonal view of an alternate embodiment of the invention; and FIG. 3B show an enlarged cross-sectional view of the sleeve of 3A.

DETAILED DESCRIPTION OF THE PREFERRED EMBODIMENT

Figure 2A:
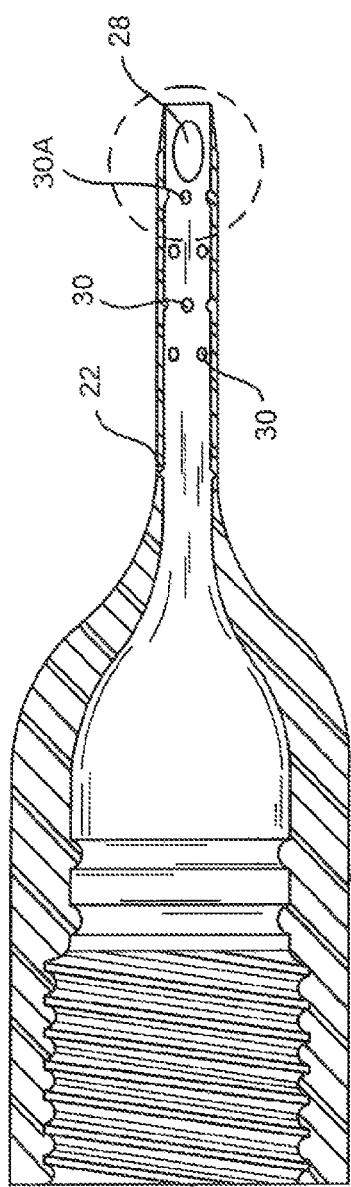
FIG. 2A shows a cross-sectional view of the sleeve of FIG. 1A.

Referring first to FIGS. 1A, 1B, 2A, 2B and 2C an apparatus 100 constructed in accordance with this invention includes a handle 10 that includes a vibrating mechanism 12 and is connected to a fluid source 14 and a vacuum source 16.

One end of the handle 10 is provided with a horn 18 terminating with a needle assembly 20 including a sleeve 22 surrounding a hollow needle 24. The needle assembly 20 narrows toward its tip as shown at 26. The sleeve 22 is formed with several ports 28. In the Figures two such ports 28 are shown disposed diametrically opposite each other.

As is typical in any phaco-emulsification apparatus, the vibration mechanism 12 produces selectively a mechanical vibration at a predetermined frequency (for example, at either a sonic, e.g. 40-400 Hz or ultrasonic, e.g. 30-60 KHz, frequency range). This vibration is transmitted through the horn 18 to the needle 24 in a known manner. The vibrating needle 24, when inserted into the anterior chamber of the eye (not shown) emulsifies or pulverizes the lens (not shown) in the anterior chamber. At the same time, irrigation fluid (typically a saline solution) from fluid source 14 passes through the sleeve 22 cooling the needle 24 and exiting through ports 28. The central passageway 25 in needle 24 is in communication with vacuum source 16. The irrigation fluid with the detritus left over the emulsification of the lens is aspired from anterior chamber through the central passageway 25 in the needle 24 in the conventional manner.

Figure 2B:
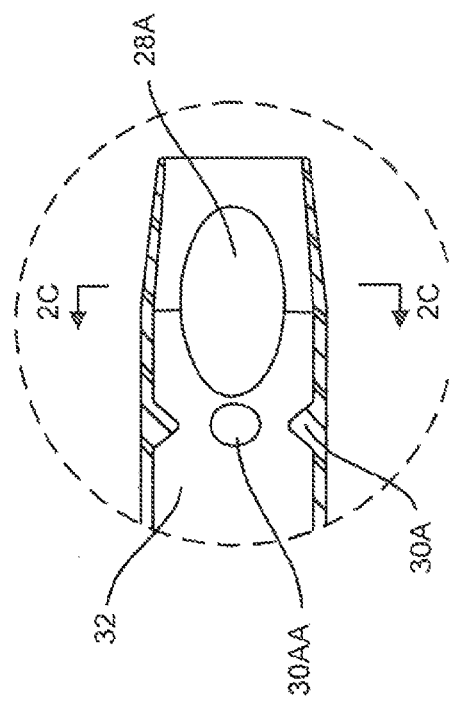
FIG. 2B shows an enlarged view of a port of the sleeve of FIG. 2A through which a liquid is ejected during a phaco-emulsification process, in accordance with this invention.
Figure 2C:
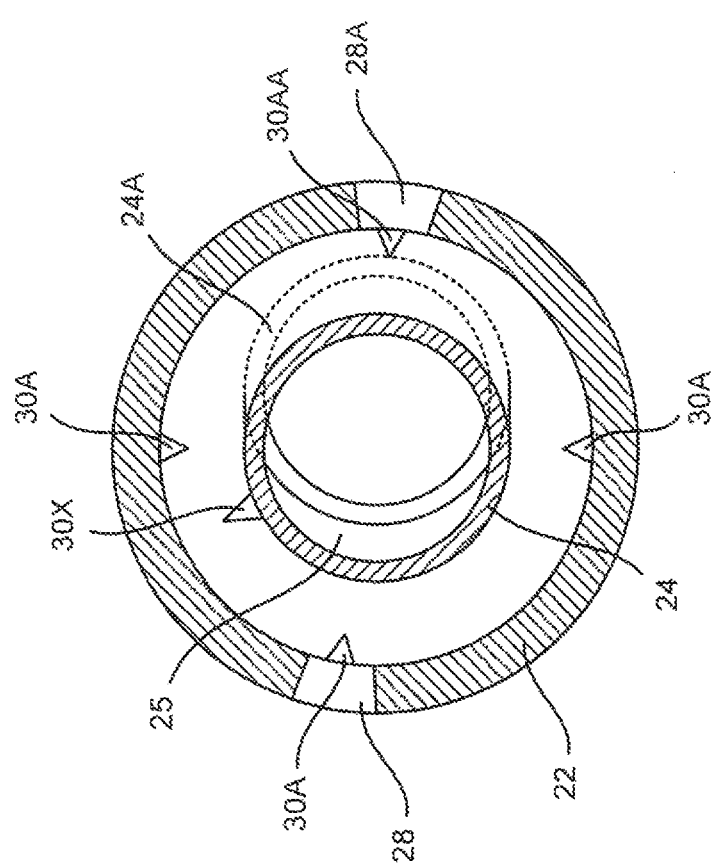
FIG. 2C shows an enlarged cross-sectional view of the sleeve and the needle taken through the ports of the sleeve.

Referring now to FIGS. 2A, 2B, 2C a problem with existing phaco-emulsification devices is that the needle disposed concentrically within the sleeve 22 (not omitted in FIGS. 2A, 2B for the sake of clarity) deflects in use and blocks at least partially ports 28. In order to prevent this phenomenon, a plurality of bumpers 30 are provided, preferably on the inner surface 32 of sleeve 22. The bumpers are made of the same material as the sleeve 22. Therefore the sleeve 22 can be made by molding or other known processes with the bumpers 30 being made integrally therewith. Preferably the bumpers 30 have a generally conical shape, although they can be other similar shapes as long as their dimension in the axial directional and circumferential direction are approximately the same.

In one embodiment, several rows of bumpers 30 are provided on the inner wall 32 of sleeve 22, positioned so as to limit the deflections of needle 24. Each row of bumpers is positioned at a predetermined axial location on sleeve 22. For example, row of bumpers 30A is disposed just slightly up stream of ports 28. Each set may include two, three or four bumpers disposed at equal angles around the inner circumference of sleeve 22. For example, the tip 26 of a typical sleeve may have the following dimensions (in inches):

Outer diameter 0.054
Thickness 0.004±0.002
Port 28 0.0056×0.0037
Height of bumpers 30 0.008
Distance of row of bumpers 30A from ports 28 0.010
Distance between bumper rows 0.050

It should be understood that these dimensions are provided only for illustrative purposes and are not meant to be interpreted as limitations.

Preferably, the rows of bumpers are arranged so that they are angularly offset from each other by 90 degrees. This arrangement is believed to be effective in controlling and limiting the deflection of needle 22. Moreover, the bumpers 30 constructed and arranged to insure that they do not interfere with the flow of the irrigation fluid through the sleeve. In other words, the bumpers are sized so that their effect on the overall cross-sectional area of the sleeve 22 is minimal and hence the sleeve 22 can have a normal or nominal size. If the bumpers are too large, or there are too many bumpers, the effective cross-sectional area of the sleeve 22 is reduced and a larger sleeve 22 would have to be used to make sure that the proper amount of irrigation liquid is provided to the anterior chamber.

As mentioned above, a problem addressed by the present invention is that during emulsification, the needle 24 tends to deflect away from its concentric position within the sleeve 22 to the point where it occludes or blocks at least partially one of the ports 28—leading to sudden changes in the flow of irrigation fluid from the ports.

However, in the sleeve 22 shown this problem is at least diminished because the deflections of the needle 24 are minimized and therefore undesirable radial oscillations of the needle 24 are minimized by bumpers 30. For example, as shown in FIG. 2C, normally needle 24 is disposed coaxially within the sleeve 22. However, during emulsification, the needle 24 deflects from its normal coaxial position, for example by deflecting towards port 28A, as indicated at 24A. However, this deflection is limited by the bumper 30AA disposed adjacent to port 28A to limit or reduce blocking of the port 28A.

FIGS. 3A and 3B show an alternate embodiment of the invention in which the sleeve 122 has a somewhat different shape then sleeve 22. However the sleeve 120 is still formed with ports 128 and bumpers 130 arranged in rows. Importantly, as can be seen in FIG. 3A, the bumpers 130 are formed in circumferential rows that are staggered in circumferential direction.

In this embodiment, the bumpers 130 have a generally cylindrical shape.

Importantly, the height of each bumper 30, i.e., its dimension in the radial direction is selected so that when needle 124 is disposed perfectly concentrically within the sleeve 122, as seen in FIG. 3B, there is a minimum distance d between each of the bumpers 130 and the needle 124. As in the previous embodiment, the reason for this feature is to insure that when the needle 124 is not deflected, e.g., when it is a neutral or coaxial position, as shown in FIG. 3B, it does not touch any of the bumpers 130. This feature insures that the sleeve 122 and the bumpers 130 do not interfere with, and attenuate the movement of the needle 124 required to perform effective phaco-emulsification. At least one bumper or a row of bumpers 130C is disposed between one of the ports 128 and the end of the sleeve 135.

In one embodiment, the distance d is constant for all the bumpers 130. Moreover the cross-sectional dimensions of all the bumpers 130 can be the same as well. In another embodiment, the dimension d and/or the cross-sectional dimension (s) of the bumpers 130 can be different. For example, bumpers 130 closer to the port 128 can be larger. For example, in FIG. 3A, the bumpers 130' distant from the port 128 have a first height H1 while the bumpers 130" closer to the port 128 have a second height H2 where H2>H1. In another embodiment, the dimension d and/or the cross-sectional dimension(s) of the bumpers can be smaller for bumpers closer to the ports 128. The choice as to whether the change these dimensions or not depends on the deflection characteristics of the needle and the amount of ballooning of sleeve 122.

In the above discussion, it has been assumed that the needle is made of titanium or other biologically inert rigid material, and that the sleeve is made of a silicone or other similar, rather flexible material that can be shaped to include the bumpers described above. Of course, the bumpers can also be placed on an outer surface of the needle, as shown at 30X in FIG. 3C. In either case the bumpers are arranged and constructed to control the lateral deflection of the needle.

Obviously numerous modifications may be made to this invention without departing from its scope as defined in the appended claims.

I claim:

1. An apparatus for performing eye surgery comprising:
a vibration mechanism;
a handle connected to a source of irrigation fluid and including a needle having a needle tip and being coupled to said vibration mechanism and adapted to be vibrated by said vibration mechanism, said handle further including an irrigation sleeve disposed around said needle and being configured for providing a path for said irrigation fluid, said sleeve having ports for ejecting said irrigation fluid and an inner surface having a generally cylindrical shape and extending in an axial direction parallel to said needle and a circumferential direction; and
a plurality of bumpers forming an array of a first set of bumpers arranged in a first ring and a second set of bumpers arranged in a second ring axially spaced with respect to said first ring, said plurality of bumpers being formed integrally on said inner surface of the sleeve, said bumpers being arranged and constructed to stabilize said needle and prevent said needle from temporarily blocking said ports during said vibration, said bumpers being sized to minimize interference with said irrigation fluid.

2. The apparatus of claim 1 wherein said bumpers are formed integrally with said sleeve.

3. The apparatus of claim 1 wherein adjacent rings of said bumpers are angularly offset from each other.

4. The apparatus of claim 1 wherein said bumpers are conical.

5. The apparatus of claim 1 wherein said bumpers are cylindrical.

6. The apparatus of claim 1 wherein said sleeve has a distal end and said bumpers are positioned between said port and said distal end.

7. The apparatus of claim 1 wherein each said bumpers has an axial dimension in said axial direction and a circumferential dimension in said circumferential direction, said axial and circumferential dimensions being substantially equal.

8. A device associated with an apparatus with a vibrating mechanism for providing surgery in the outside or within capsular bag of an eye, said apparatus comprising:

an elongated sleeve terminating at a distal end with a tip and being adapted to couple to said vibrating mechanism, said elongated sleeve being adapted to conducted irrigation fluid to the eye through at least two ports;

a needle disposed in said sleeve and coupled to the vibration mechanism and adapted to vibrate; and a plurality of bumpers forming an array of a first set of bumpers arranged in a first ring and a second set of bumpers arranged in a second ring axially spaced with respect to said first ring, said plurality of bumpers being formed integrally on said inner surface of the sleeve, said bumpers being arranged and constructed to stabilize said needle and prevent said needle from temporarily blocking said ports during said vibration, said bumpers being sized to minimize interference with said irrigation fluid.

9. The device of claim 8 wherein said ports are spaced longitudinally away from said tip.

10. The device of claim 8 wherein said bumpers have different heights.

11. The device of claim 8 wherein each said bumpers has an axial dimension in said axial direction and a circumferential dimension in said circumferential direction, said axial and circumferential dimensions being substantially equal.

\* \* \* \* \*